(12) United States Patent
Farazi

(10) Patent No.: US 9,095,719 B2
(45) Date of Patent: Aug. 4, 2015

(54) IMPLANTABLE DEVICE WITH RESPONSIVE VASCULAR AND CARDIAC CONTROLLERS

(71) Applicant: Pacesetter, Inc., Sunnyvale, CA (US)

(72) Inventor: Taraneh Ghaffari Farazi, San Jose, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 0 days.

(21) Appl. No.: 14/165,341

(22) Filed: Jan. 27, 2014

(65) Prior Publication Data

US 2014/0316480 A1    Oct. 23, 2014

Related U.S. Application Data

(62) Division of application No. 10/972,278, filed on Oct. 21, 2004, now Pat. No. 8,676,326.

(51) Int. Cl.
| | |
|---|---|
| *A61N 1/365* | (2006.01) |
| *A61N 1/05* | (2006.01) |
| *A61N 1/36* | (2006.01) |
| *A61N 1/368* | (2006.01) |

(52) U.S. Cl.
CPC ............ *A61N 1/36585* (2013.01); *A61N 1/056* (2013.01); *A61N 1/0551* (2013.01); *A61N 1/368* (2013.01); *A61N 1/36057* (2013.01); *A61N 1/36114* (2013.01)

(58) Field of Classification Search
USPC ............................................ 607/9, 17, 23, 44
See application file for complete search history.

(56) References Cited

U.S. PATENT DOCUMENTS

| | | |
|---|---|---|
| 5,330,507 A | 7/1994 | Schwartz |
| 5,458,626 A | 10/1995 | Krause |
| 5,700,282 A | 12/1997 | Zabara |
| 6,473,644 B1 | 10/2002 | Terry |
| 6,625,493 B2 | 9/2003 | Kroll |

(Continued)

FOREIGN PATENT DOCUMENTS

WO    WO 03041559    5/2003

OTHER PUBLICATIONS

Non-Final Office Action mailed Dec. 29, 2006: Related U.S. Appl. No. 10/972,278.

(Continued)

*Primary Examiner* — Deborah Malamud
(74) *Attorney, Agent, or Firm* — Theresa A. Raymer

(57) ABSTRACT

Exemplary methods are described for providing responsive vascular control with or without cardiac pacing. An implantable device with responsive vascular and cardiac controllers interprets physiological conditions and responds with an appropriate degree of vascular therapy applied as electrical pulses to a sympathetic nerve. In one implementation, an implantable device is programmed to deliver the vascular therapy in response to low blood pressure or orthostatic hypotension. The device may stimulate the greater splanchnic nerve, to effect therapeutic vasoconstriction. The vascular therapy is dynamically adjusted as the condition improves. In one implementation to benefit impaired physical mobility, vascular therapy comprises vasoconstriction and is timed to coincide with a recurring segment of the cardiac cycle. The vasoconstriction assists circulation and venous return in the lower limbs of inactive and bedridden individuals. In various implementations, cardiac pacing therapy that is synergistic with the vascular therapy may be added to augment treatment.

20 Claims, 8 Drawing Sheets

(56) References Cited

U.S. PATENT DOCUMENTS

| | | |
|---|---|---|
| 6,658,292 B2 | 12/2003 | Kroll |
| 6,662,047 B2 | 12/2003 | Sorensen |
| 6,937,896 B1 | 8/2005 | Kroll |
| 7,373,204 B2 | 5/2008 | Gelfand |
| 2002/0147475 A1 | 10/2002 | Scheiner |
| 2002/0147476 A1 | 10/2002 | Daum |
| 2003/0040778 A1 | 2/2003 | Kroll |
| 2003/0045909 A1 | 3/2003 | Gross |
| 2003/0045910 A1 | 3/2003 | Sorensen |
| 2003/0060857 A1 | 3/2003 | Perrson |
| 2005/0288718 A1 | 12/2005 | Sunagawa |
| 2006/0116721 A1 | 6/2006 | Yun |

OTHER PUBLICATIONS

Final Office Action mailed Oct. 4, 2007: Related U.S. Appl. No. 10/972,278.

Non-Final Office Action mailed Mar. 4, 2008: Related U.S. Appl. No. 10/972,278.

Final Office Action mailed Nov. 17, 2008: Related U.S. Appl. No. 10/972,278.

Advisory Action mailed Feb. 10, 2009: Related U.S. Appl. No. 10/972,278.

Non-Final Office Action mailed Mar. 17, 2010: Related U.S. Appl. No. 10/972,278.

Final Office Action mailed Aug. 6, 2010: Related U.S. Appl. No. 10/972,278.

Notice of Allowance mailed Nov. 27, 2013: Related U.S. Appl. No. 10/972,278.

IMPLANTABLE DEVICE WITH RESPONSIVE VASCULAR AND CARDIAC CONTROLLERS

PRIORITY CLAIM

This application is a Divisional application of U.S. patent application Ser. No. 10/972,278, filed Oct. 21, 2004 entitled "IMPLANTABLE DEVICE WITH RESPONSIVE VASCULAR AND CARDIAC CONTROLLERS" which is incorporated herein by reference in its entirety to provide continuity of disclosure.

TECHNICAL FIELD

Subject matter presented herein generally relates to implantable medical devices and more particularly to an implantable device with responsive vascular and cardiac controllers.

BACKGROUND

Conventionally, implantable cardiac devices (ICDs), including "pacemakers," have emphasized stimulating the heart. The heart is situated in a single location in the body so it is relatively easy to place an ICD in close proximity to cardiac muscle tissue. The human vascular system, on the other hand, includes vast networks of blood vessels that are spread pervasively throughout the body, so it is relatively difficult to gain ICD control of vascular muscle tissue in the linings of arteries and veins.

Conventional ICDs have avoided or ignored controlling the vascular muscle layers of arteries and veins for additional reasons. Cardiac muscle tissue differs from both skeletal muscle tissue and smooth muscle tissue by being quickly responsive to electrical stimulation, whereas the smooth muscle tissue surrounding arteries and veins is relatively slow to react. Conventional circulatory control was easily achieved by stimulating the responsive and easily accessible cardiac muscle tissue, with its largely self-contained electrical system. The smooth muscle tissue of the vascular system, by comparison, was more difficult to access and control.

The smooth muscle layers of arteries are controlled by the sympathetic and parasympathetic nervous subsystems with control often originating in the brain, yet not under direct conscious control. A host of hormones and pharmaceuticals that bind to receptors on smooth muscles and exert their own influences can interfere with artificial electrical control of these smooth muscle layers.

When the body controls its own vascular system, the aforementioned layer of smooth muscle between elastic lamina (layers) of an artery typically opens and closes the bore or "lumen" of the artery. Closing an arterial lumen is referred to as vasoconstriction, which typically increases blood pressure because the circulatory system has a relatively inflexible volume capacity. Opening an arterial lumen is referred to as vasodilation and typically lowers the blood pressure.

Control over the same parameters that are ubiquitously present in many artificial hydraulic systems can lead to more masterful treatment of human circulatory diseases as well. To treat hypertension (high blood pressure) or hypotension (low blood pressure) for example, treatments include control over the heart as pump, over the volume capacity of the system (for example, using diuretics), and/or over the volume of fluid in the system. By nature, a human body in good health controls these three factors simultaneously. For example, when increased blood perfusion is needed for physical exertion, the body may deliver more blood to the exercising tissues by simultaneously increasing the strength and speed of the pumping action and raising the blood pressure, by vasoconstriction.

The sympathetic and parasympathetic subsystems, which initiate vasoconstriction and vasodilation respectively, are not limited to controlling mere low-level operational aspects of the body corresponding to valves and sensors in a hydraulic machine. Rather, these nervous subsystems also play more profound roles in directing activities of daily living and emotions. During rest times, for example, vasodilation maintained by the parasympathetic subsystem may direct more blood to activities like digestion, with resultant feelings of relaxation, while during physical activity and stress, vasoconstriction initiated by the sympathetic subsystem may direct blood away from the digestive tract to skeletal muscles, with resultant feelings of strength and excitement.

Comprehensive control of the circulatory system, such as that accomplished by the body itself, can provide improved treatment for many circulatory maladies. For example, orthostatic hypotension (OSH) is a common geriatric disorder as well as a common side effect of many medications. It is generally described as a decrease of 10-20 millimeters of mercury (mmHg) or more in systolic blood pressure when posture changes from supine to standing—a horizontal to vertical change in posture. OSH can have neurogenic etiologies (e.g., diminished baroreceptor reflex); vestibular disorders; peripheral/central nervous system deficiencies; etc.) or non-neurogenic etiologies (e.g., cardiac pump failure, reduced blood volume, venous pooling, etc.). Device therapies that only elevate heart rate during an OSH episode (i.e., that target the non-neurogenic deficiencies) may fail if there is a lack of vasoconstriction due to reduced baroreceptor reflex. Similarly, treatments that only stimulate vasomotor sympathetic nerves (i.e., target only neurogenic deficiencies) may fail if there is a pronounced pumping failure. Thus, an implantable medical device therapy that can simultaneously compensate for both neurogenic and non-neurogenic influences on the circulatory system can be very advantageous in treating OSH and other disorders.

There is a need for an implantable device that takes advantage of the autonomic nervous system, resulting in simultaneous control of more types of muscle tissues in the circulatory system than just cardiac muscle tissue. Such an implantable device would control the cardio and vascular components of the cardiovascular system in a more organic and comprehensive manner than just controlling heart rate and other cardiac parameters via a conventional ICD.

SUMMARY

Implantable devices and methods are described for providing responsive vascular control with or without cardiac pacing. An implantable device with responsive vascular and cardiac controllers interprets physiological conditions and responds with an appropriate degree of vascular therapy applied as electrical pulses to a sympathetic nerve. In one implementation, an implantable device is programmed to deliver the vascular therapy in response to low blood pressure or orthostatic hypotension. The device may stimulate the greater splanchnic nerve, to effect therapeutic vasoconstriction. The vascular therapy is dynamically adjusted as the condition improves.

In one implementation that is capable of benefiting a person afflicted with impaired physical mobility, the vascular therapy to be applied comprises vasoconstriction, especially in the arteries of the lower limbs, and is timed to coincide with a recurring segment of each cardiac cycle, that is, many times per minute. The vasoconstriction is timed to occur just as blood pressure is dropping between systole and diastole—to give the contraction of elastic arterial walls extra force. This provides reinforcement for blood transport in the lower limbs of an inactive person, augmenting venous return.

In various implementations, cardiac pacing therapy that is synergistic with the vascular therapy may be added to augment treatment. The added cardiac pacing therapy may base values for cardiac pacing parameters on the magnitude of current vascular stimulation parameters. If cardiac therapy is added, then both the vascular therapy and the cardiac therapy can be dynamically adjusted through feedback from physiological sensors as conditions improve.

DETAILED DESCRIPTION

Overview

Figure 1:
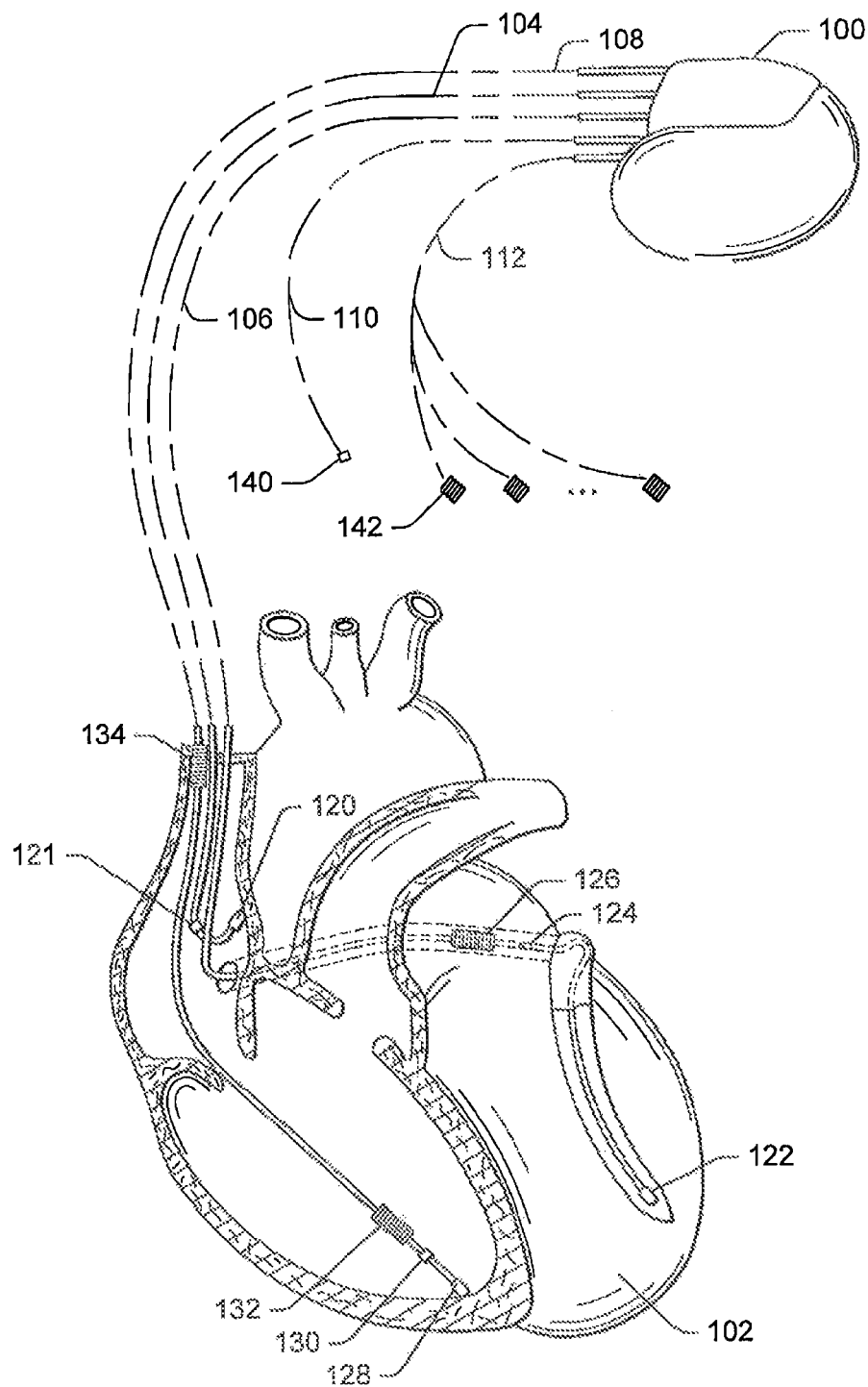
FIG. 1 is a diagram illustrating an exemplary implantable device in electrical communication with a human heart.

The following discussion describes an exemplary implantable device ("device") that includes a responsive cardiovascular controller. The device can exert artificial vasomotor control and artificial cardiac control, with both cardio control and vascular control responsive to each other and to feedback from physiological sensors. In one implementation, the device is capable of monitoring changes in postures and blood pressure, and responding to these physiological variables by exerting vasomotor control, monitoring cardiac activity, and providing cardiac pacing when needed. The device includes feedback control mechanisms that can determine the level and duration of vasomotor stimulation to apply with or without cardiac pacing to achieve appropriate vasoconstriction, cardiac pumping, and blood pressure.

In one implementation, the implantable device can control vascular tone (and cardiac pacing) in dynamic response to orthostatic hypotension. In another or the same implementation, the implantable device can control vascular tone to assist blood flow in the extremities of a bedridden person, in response to the physiological parameter of impaired physical mobility. In these implementations a cardiac stimulator can be included to augment and reinforce control of vascular tone by additionally controlling heart rate and/or other cardiac parameters.

The aforementioned orthostatic hypotension results when a susceptible person assumes an upright position so that the head and brain, being at the highest aspect of a hydrostatic column of fluid, suffer low blood pressure causing lightheadedness and even loss of consciousness. The sympathetic nervous system normally senses the change in blood pressure and compensates by reflexively constricting blood vessels to increase system pressure. Conventional techniques that compensate for orthostatic hypotension have been proposed, for example, in U.S. Pat. No. 4,791,931 to Slate, entitled, "Demand pacemaker using an artificial baroreceptor reflex." The Slate technique, however, increases only heart rate to compensate for low blood pressure. A natural baroreceptor reflex also increases vascular tone in response to intracranial blood pressure that has decreased too quickly. This vasoconstriction decreases the volume of the arterial circulatory system thereby increasing fluid pressure to the head.

Some individuals lack a normal baroreceptor reflex so that a conventional technique, such as that described by Slate—of increasing heart rate to compensate for orthostatic hypotension—is not effective. Implementations of the implantable device described herein can sense changes in blood pressure through conventional methods and, being alerted to an undesirable condition, can initiate a compensatory change in vascular tone that is proportional to the initial degree of blood pressure change and dynamically maintain treatment for ongoing variations thereafter. Moreover, blood pressure sensing—or more broadly, sensing of a physiologic variable—and the responsive vascular tone control are coupled in a feedback loop that models the human body's own feedback mechanisms for regulating body systems and maintaining physiological homeostasis. Since the implantable device can control vascular tone, various alternative implementations of the device may be used to assist blood flow in bedridden individuals or provide therapy for other vascular conditions, such as peripheral vascular disease of diabetes, vasovagal syncope, post-fracture swelling of a limb due to lack of muscular and vascular tone after casting, etc.

Exemplary Implantable Device

FIG. 1 shows an exemplary implementation of the device 100 introduced above in electrical communication with a human heart 102 and other bodily tissues. Such an exemplary device 100 can be characterized as a miniature computing device that is implanted into a body to monitor, regulate, and/or correct cardiovascular and other activities. The device 100 may be an ICD (e.g., implantable cardiac pacemaker, implantable defibrillator, etc.) that applies stimulation therapy to the heart or may be another type of implantable device that can perform the responsive cardiovascular techniques described herein. In the illustrated implementation, three of the electrical leads-a right atrial lead 104, a coronary sinus lead 106, and a right ventricular lead 108—interconnect the device 100 with the heart 102 to support multi-chamber detection and stimulation therapy. One or more physiological sensor lead(s) 110 may also be employed to position physiological sensors within the body and a vascular stimulation lead 112 may be used to position electrodes to facilitate stimulation of vascular tissue or nervous tissue that innervates a vascular bed.

The right atrial lead 104 supports an atrial tip electrode 120, which is typically implanted in a patient's right atrial appendage. The right atrial lead 104 also supports a right atrial ring electrode 121, which enables the device to sense atrial cardiac signals and apply pacing therapy to the right atrial chamber.

The coronary sinus lead 106 positions a left ventricular tip electrode 122 adjacent to the left ventricle and/or additional electrode(s) adjacent to the left atrium, such as a left atrial ring electrode 124 and a left atrial coil electrode 126. The coronary sinus lead 106 enables the exemplary device 100 to sense left atrial and ventricular cardiac signals and administer left chamber pacing therapy. In the illustrated arrangement, the left ventricular tip electrode 122 is used to sense atrial and ventricular cardiac signals and deliver left ventricular pacing therapy. The left atrial ring electrode 124 is employed for applying left atrial pacing therapy, and the left atrial coil electrode 126 may be used for shocking therapy.

The right ventricular lead 108 is electrically coupled to a right ventricular tip electrode 128, a right ventricular ring electrode 130, a right ventricular (RV) coil electrode 132, and a superior vena cava (SVC) coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of receiving cardiac signals, and delivering stimulation in the form of pacing and shock therapy to the right ventricle.

One or more physiological sensor lead(s) 110 may be positioned to allow a physiological sensor 140, such as a blood pressure probe, to come in contact with the patient's blood, nerve tissue, or other bodily part. In the case of a blood pressure probe, a photoplethysmograph (PPG) infrared light sensor may be coupled to the physiological sensor lead 110.

A vascular stimulation lead 112 may be positioned to facilitate stimulation of vascular tissue or nervous tissue that innervates a vascular bed. The nervous tissue may be a sympathetic efferent nerve, such as the greater splanchnic nerve. If one or more sympathetic nerves are to be stimulated to control vascular tone, then one or more cuff electrodes 142 may be used to couple the vascular stimulation lead 112 to the nerve tissue.

Figure 2:
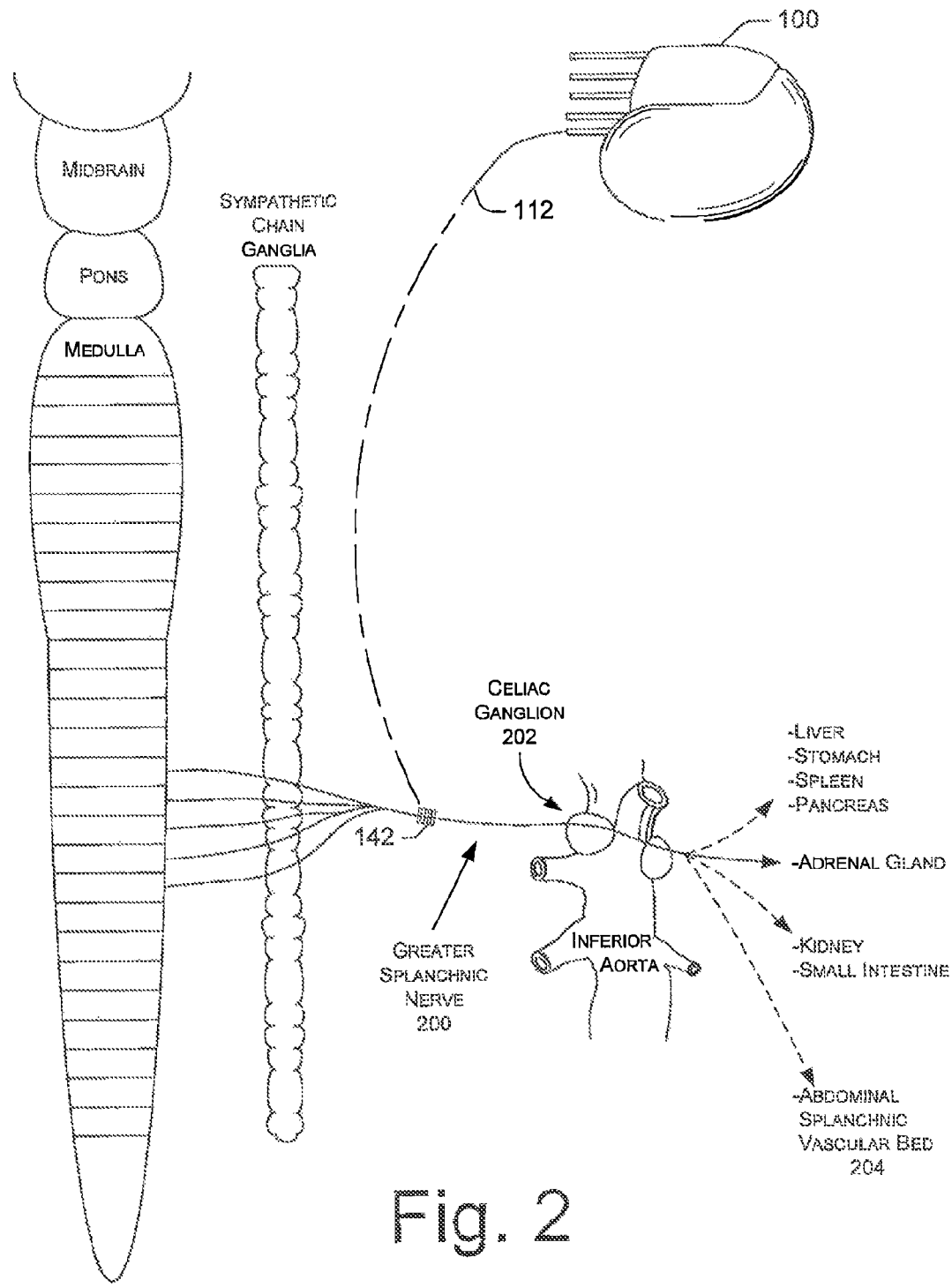
FIG. 2 is a diagram illustrating the exemplary implantable device in electrical communication with a human greater splanchnic nerve.

FIG. 2 shows an exemplary placement of a cuff electrode 142 on a sympathetic nerve, such as the greater splanchnic nerve 200, to stimulate the nerve and achieve a vasomotor response.

The greater splanchnic nerve 200 is the preganglionic sympathetic innervation to the celiac ganglia 202, which typically lie on or straddle the Inferior aorta. The celiac ganglia 202 lie on the left and right sides of the celiac trunk at its origin and are in contact with the surface of the aorta. They are the largest of the sympathetic ganglia that are located on the aorta's surface. The celiac ganglia 202 innervate various abdominal organs and glands (e.g., the liver, stomach, pancreas, kidneys, and small intestine). It should be noted that nerve impulses through sympathetic fibers to these visceral organs generally inhibit the activity of the organs. The celiac ganglia 202 also provide innervation to the adrenal glands and to the abdominal splanchnic vascular bed 204. This vascular bed may be the major effector mechanism for the arterial baroreflex. That is, in a healthy individual, low blood pressure triggers a baroreceptor reflex that sends sympathetic nerve impulses to the adrenal glands and to the abdominal splanchnic vascular bed 204 in order to compensate for the low blood pressure. The compensation likely comprises a global vasoconstriction of the vessels in the abdominal splanchnic vascular bed 204 and a release of epinephrine from the adrenal glands.

The release of epinephrine (adrenaline) into the circulatory system in response to splanchnic nerve stimulation produces a pronounced global sympathetic effect that causes vasoconstriction and increases blood pressure in most parts of the body almost instantaneously. Thus, by stimulating the greater splanchnic nerve 200, the device 100 effects a vasomotor response electrically, mechanically (through vasoconstriction), and chemically (through release of epinephrine).

Figure 3:
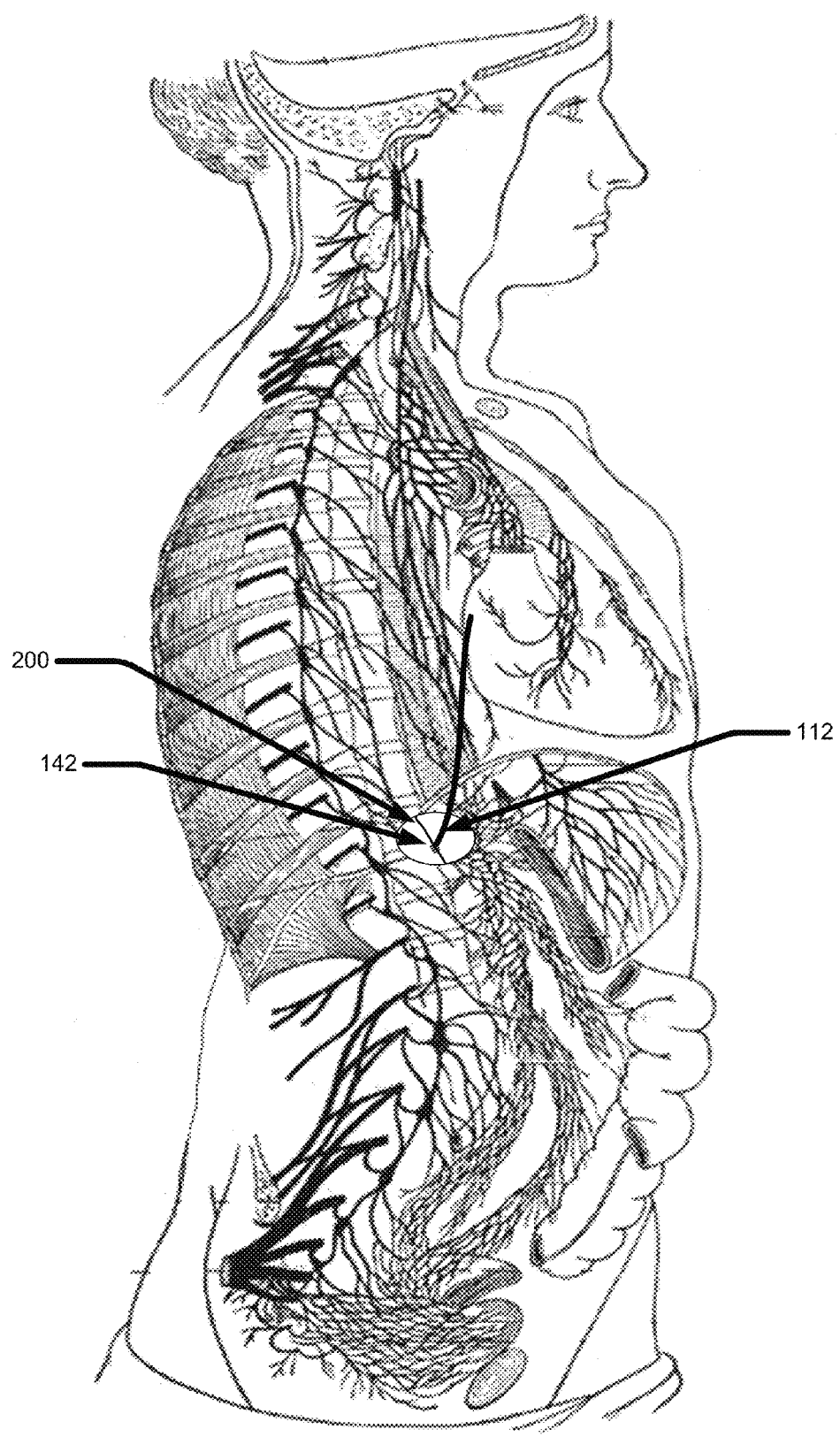
FIG. 3 is a diagram illustrating the relative bodily position of a cuff electrode of the exemplary implantable device around the greater splanchnic nerve.

FIG. 3 shows an exemplary placement of the vascular stimulation lead 112 in relation to other aspects of the human body. A cuff electrode 142 is shown surgically placed around the greater splanchnic nerve 200. The vascular stimulation lead 112, or course, couples one or more cuff electrodes 142 with the device 100 (not shown, because the device 100 may be placed in various locations, for example, it may even be placed in the abdomen).

Figure 4:
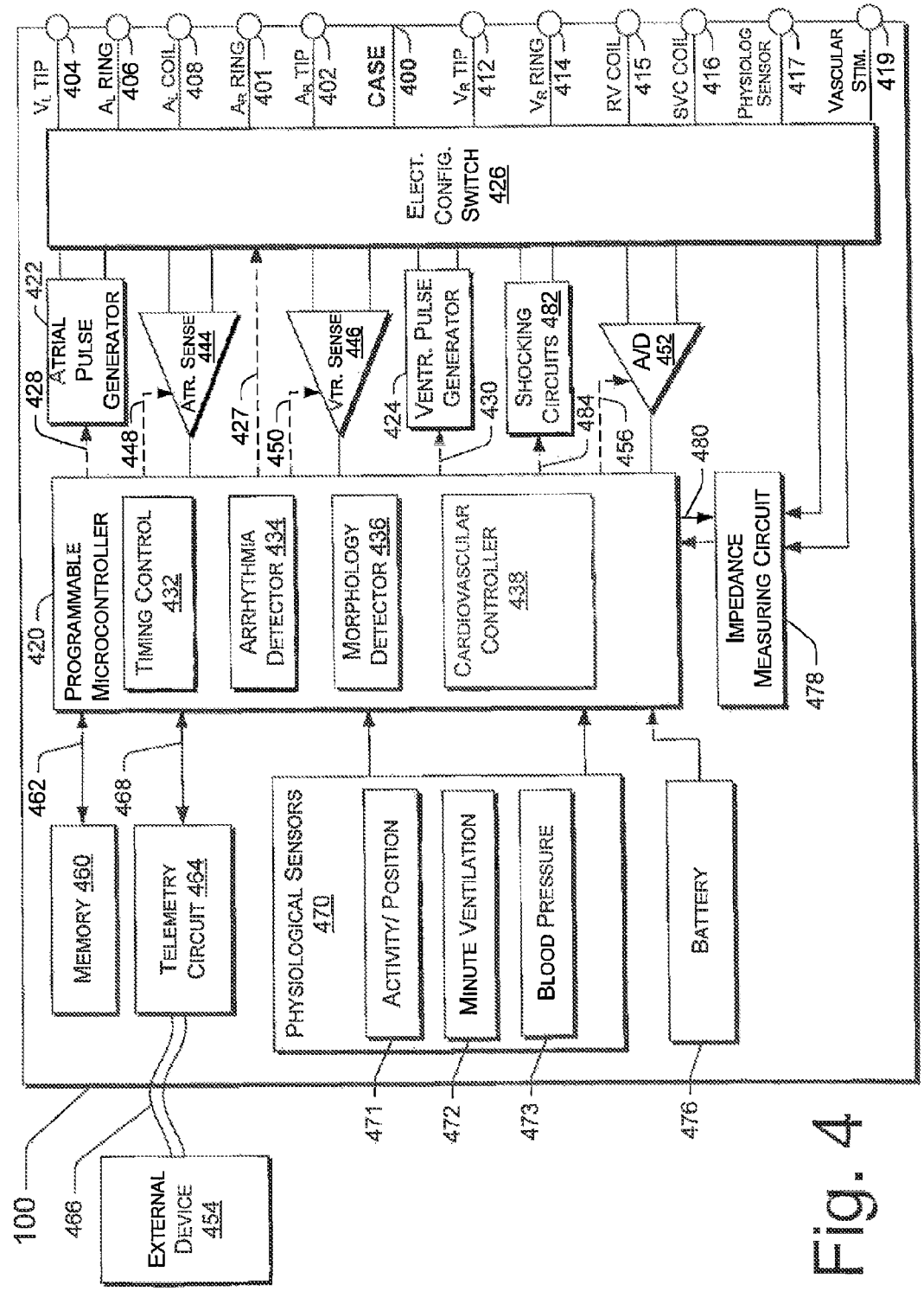
FIG. 4 is block diagram of an exemplary implementation of the exemplary implantable device.

FIG. 4 shows an exemplary block diagram depicting various components of the device 100. The components are typically contained in a case 400, which is often referred to as the "can", "housing", "encasing", or "case electrode", and may be programmably selected to act as the return electrode for unipolar operational modes. The case 400 may further be used as a return electrode alone or in combination with one or more of the coil electrodes 126, 132 and 134 for stimulating purposes. The case 400 further includes a connector (not shown) having a plurality of terminals (401, 402, 404, 406, 408, 412, 414, 415, 416, 417, and 419—shown schematically with the names of the electrodes to which they are connected shown next to the terminals), including:

a right atrial ring terminal (AR RING) 401 for atrial ring electrode 121;
a right atrial tip terminal (AR TIP) 402 for atrial tip electrode 120;
a left ventricular tip terminal (VL TIP) 404 for left ventricular tip electrode 122;
a left atrial ring terminal (AL RING) 406 for left atrial ring electrode 124;
a left atrial shocking terminal (AL COIL) 408 for left atrial coil electrode 126;
a right ventricular tip terminal (VR TIP) 412 for right ventricular tip electrode 128;
a right ventricular ring terminal (VR RING) 414 for right ventricular ring electrode 130;
a right ventricular shocking terminal (RV COIL) 415 for RV coil electrode 132;
an SVC shocking terminal (SVC COIL) 416 for SVC coil electrode 134;
a physiological sensor terminal 417 for physiological sensor 140, e.g., a blood pressure probe; and
a vascular stimulation terminal 419 for coupling with a vascular stimulation lead 112 and cuff electrode.

An exemplary device 100 may include a programmable microcontroller 420 that controls various operations of the implantable cardiac device, including cardiac monitoring and cardiovascular stimulation therapy. Microcontroller 420 includes a microprocessor (or equivalent control circuitry), RAM and/or ROM memory, logic and timing circuitry, state machine circuitry, and I/O circuitry.

Exemplary device 100 further includes an atrial pulse generator 422 and a ventricular pulse generator 424 that generate pacing stimulation pulses for delivery by the right atrial lead 104, the coronary sinus lead 106, and/or the right ventricular lead 108 via an electrode configuration switch 426. The electrode configuration switch 426 may include multiple switches for connecting the desired electrodes to the appropriate I/O circuits, thereby providing complete electrode programmability. Accordingly, switch 426, in response to a control signal 427 from the microcontroller 420, determines the polarity of the stimulation pulses (e.g., unipolar, bipolar, etc.) by selectively closing the appropriate combination of switches.

To provide stimulation therapy in each of the four chambers of the heart, the atrial and ventricular pulse generators 422 and 424 may include dedicated, independent pulse generators, multiplexed pulse generators, or shared pulse generators. The pulse generators 422 and 424 are controlled by the microcontroller 420 via appropriate control signals 428 and 430, respectively, to trigger or inhibit the stimulation pulses.

Microcontroller 420 is illustrated as including timing control circuitry 432 to control the timing of the stimulation pulses (e.g., pacing rate, atrioventricular (AV) delay, atrial interconduction (A-A) delay, or ventricular interconduction (V-V) delay, native atrial event to native or stimulated ventricular event (PV) delay, (AV/PV) delay, etc.). The timing control circuitry may also be used for the timing of refractory periods, blanking intervals, noise detection windows, evoked response windows, alert intervals, marker channel timing, and so on.

Microcontroller 420 may also implement an arrhythmia detector 434, a morphology detector 436, and an exemplary cardiovascular controller 438. The cardiovascular controller 438 in turn can process input from physiological sensors 470, such as accelerometers and a blood pressure sensor 473, diagnose cardiovascular disturbances, such as orthostatic hypotension, and provide cardiovascular therapies. The therapies may compensate for detected cardiovascular disturbances using ongoing feedback from the physiological sensors 470. The cardiovascular controller 438 can also provide synergistic vascular and cardiac therapies.

The components 434, 436, and 438 may be implemented in hardware as part of the microcontroller 420, or as software/firmware instructions programmed into an implementation of the device 100 and executed on the microcontroller 420 during certain modes of operation. Although not shown, the microcontroller 420 may further include other dedicated circuitry and/or firmware/software components that assist in monitoring various conditions of the patient's heart and managing pacing therapies.

Atrial sensing circuits 444 and ventricular sensing circuits 446 may also be selectively coupled to the right atrial lead 104, coronary sinus lead 106, and the right ventricular lead 108, through the switch 426 to detect the presence of cardiac activity in each of the four chambers of the heart. The sensing circuits 444 and 446 may include dedicated sense amplifiers, multiplexed amplifiers, or shared amplifiers. Switch 426 determines the "sensing polarity" of the cardiac signal by selectively closing the appropriate switches. In this way, the clinician may program the sensing polarity independent of the stimulation polarity.

Each sensing circuit 444 and 446 may employ one or more low power precision amplifiers with programmable gain and/or automatic gain control, bandpass filtering, and a threshold detection circuit to selectively sense the cardiac signal of interest. The automatic gain control enables the exemplary device 100 to sense low amplitude signal characteristics of atrial or ventricular fibrillation.

The outputs of the atrial and ventricular sensing circuits 444 and 446 are connected to the microcontroller 420 which, in turn, is able to trigger or inhibit the atrial and ventricular pulse generators 422 and 424 in a demand fashion in response to the absence or presence of cardiac activity in the appropriate chambers of the heart. The sensing circuits 444 and 446 receive control signals from the microcontroller 420 over signal lines 448 and 450 to control, for example, the gain and/or threshold of polarization charge removal circuitry (not shown) and the timing of blocking circuitry (not shown) optionally coupled to the inputs of the sensing circuits 444, 446.

Cardiac signals are supplied to an analog-to-digital (A/D) data acquisition system 452, which is configured to acquire intracardiac electrogram signals, convert the raw analog data into a digital signal, and store the digital signals for later processing and/or telemetric transmission to an external device 454. The data acquisition system 452 is coupled to the right atrial lead 104, the coronary sinus lead 106, and the right ventricular lead 108 through the switch 426 to sample cardiac signals across any pair of desired electrodes.

The data acquisition system 452 is coupled to the microcontroller 420, or other detection circuitry, to assist in detecting an evoked response from the heart 102 in response to an applied stimulus, which is often referred to as detecting "capture". Capture occurs when an electrical stimulus applied to the heart is of sufficient energy to depolarize the cardiac tissue, thereby causing the heart muscle to contract. The microcontroller 420 detects a depolarization signal during a window following a stimulation pulse, the presence of which indicates that capture has occurred. The microcontroller 420 enables capture detection by triggering the ventricular pulse generator 424 to generate a stimulation pulse, starting a capture detection window using the timing control circuitry 432 within the microcontroller 420, and enabling the data acquisition system 452 via control signal 456 to sample the cardiac signal that falls in the capture detection window and, based on the amplitude, determines if capture has occurred.

The microcontroller 420 is further coupled to a memory 460 by a suitable data/address bus 462. The programmable operating parameters used by the microcontroller 420 are stored in memory 460 and used to customize the operation of the exemplary device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 102 within each respective tier of therapy.

The operating parameters of the exemplary device 100 may be non-invasively programmed into the memory 460 through a telemetry circuit 464 in telemetric communication via communication link 466 with the external device 454, such as a programmer, local transceiver, or a diagnostic system analyzer. The microcontroller 420 can activate the telemetry circuit 464 with a control signal 468. The telemetry circuit 464 allows intracardiac electrograms and status information relating to the operation of the exemplary device 100 (as contained in the microcontroller 420 or memory 460) to be sent to the external device 454 through an established communication link 466.

The physiological sensors 470 referred to above can further include, for example, "rate-responsive" sensors that adjust pacing stimulation rates according to the exercise state of the patient. Accordingly, the microcontroller 420 responds by adjusting the various pacing parameters (such as rate, AV Delay, V-V Delay, etc.) at which the atrial and ventricular pulse generators 422 and 424 generate stimulation pulses.

The physiological sensors 470 may include mechanisms and sensors to detect bodily movement, changes in cardiac output, changes in the physiological condition of the heart, diurnal changes in activity (e.g., detecting sleep and wake states), G-force acceleration of the pacemaker case 400, length of the cardiac QT interval, blood oxygen saturation, blood pH, changes in blood pressure, changes in temperature, respiration rate, and QRS wave duration. While shown as being included within the exemplary device 100, the physiological sensor(s) 470 may also be external to the exemplary device 100, yet still be implanted within or carried by the patient, e.g., a blood pressure probe. Examples of physiological sensors external to the case 400 that may be deployed by device 100 include sensors that, for example, sense respiration activities, O2 saturation, evoked response, pH of blood, and so forth.

The illustrated physiological sensors 470 include one or more activity/position sensors 471 (e.g., 1D or 3D accelerometers, movement sensors, etc.) to detect changes in the patient's position. The activity/position sensors 471 can be used by a cardiovascular controller 438 to assist detection of orthostatic hypotension caused by transition from a less upright posture to a comparatively more upright posture. One example postural change leading to orthostatic hypotension in susceptible individuals is a movement from a supine position in a rest state (e.g., sleeping in bed) to an upright position in a non-rest state (e.g., sitting or standing up). In response to the detected postural change, a cardiovascular controller 438 may evaluate blood pressure to see if there has been a decrease in the blood pressure sustained for a duration that is longer than that which usually transpires before a healthy baroreceptor reflex intervenes. The cardiovascular controller 438 may then administer one or more vascular and/or pacing therapies to reduce the orthostatic hypotension.

In one configuration, accelerometer output signal is bandpass-filtered, rectified, and integrated at regular timed intervals. A processed accelerometer signal can be used as a raw activity signal. The device derives an activity measurement based on the raw activity signal at intervals timed according to the cardiac cycle. The activity signal alone can be used to indicate whether a patient is active or resting. The activity measurement can further be used to determine an activity variance parameter. A large activity variance signal is indicative of a prolonged exercise state. Low activity and activity variance signals are indicative of a prolonged resting or inactivity state. The activity variance can be monitored diurnally to detect the low variance in the measurement corresponding to the sleep state. For a complete description of the activity variance sensor, the reader is directed to U.S. Pat. No. 5,476,483 (Bomzin et al.), issued Dec. 19, 1995, which is hereby incorporated by reference.

Other illustrated physiological sensors 470 include one or more blood pressure sensors 473, such as a photoplethysmograph (PPG) infrared light sensor surface mounted on the case 400 or external to the device 100. Thus, signals generated by the physiological sensors 470 can be passed to the microcontroller 420 for analysis by the cardiovascular controller 438. Such signals can be used to determine whether the patient is at rest, whether the patient is experiencing an episode of orthostatic hypotension or other cardiovascular disturbance and whether to invoke any responsive therapy prescribed by the cardiovascular controller 438.

A minute ventilation (MV) sensor 472 may also be included in the physiological sensors 470 in order to sense rate and depth of breathing. Minute ventilation can be measured as the total volume of air that moves in and out of a patient's lungs in a minute. The MV sensor 472 may use transthoracic impedance, which is a measure of impedance across the chest cavity, to sense air movement.

The exemplary device 100 additionally includes a battery 476 that provides operating power to all of the components shown in FIG. 4. The battery 476 is capable of operating at low current drains for long periods of time (e.g., less than 10 µA), and is capable of providing high-current pulses (for capacitor charging) when the patient requires a shock pulse (e.g., in excess of 2 A, at voltages above 2 V, for periods of 10 seconds or more). The battery 476 also desirably has predictable discharge characteristics so that elective replacement time can be detected. As one example, the exemplary device 100 employs lithium/silver vanadium oxide batteries.

The exemplary device 100 can further include magnet detection circuitry (not shown), coupled to the microcontroller 420, to detect when a magnet is placed over the exemplary device 100. A magnet may be used by a clinician to perform various test functions of the exemplary device 100 and/or to signal the microcontroller 420 that an external programmer (e.g., 454) is in place to receive or transmit data to the microcontroller 420 through the telemetry circuits 464.

The exemplary device 100 further includes an impedance measuring circuit 478 that is enabled by the microcontroller 420 via a control signal 480. The impedance measuring circuit 478 is used for many things, including: lead impedance surveillance during acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring cardiac stroke volume; detecting the opening of heart valves; and so forth. The impedance measuring circuit 478 may be coupled to the switch 426 so that any desired electrode may be used.

The exemplary device 100 may be operated as an implantable cardioverter/defibrillator device, which detects the occurrence of an arrhythmia and automatically applies an appropriate electrical shock therapy to the heart aimed at terminating the detected arrhythmia. To this end, the microcontroller 420 further controls a shocking circuit 482 via a control signal 484. The shocking circuit 482 generates shocking pulses of low (e.g., up to 0.5 joules), moderate (e.g., 0.5-10 joules), or high energy (e.g., 11 to 40 joules), as selected by the microcontroller 420. Such shocking pulses are applied to the patient's heart 102 through at least two shocking electrodes selected, for example, from the left atrial coil electrode 126, the RV coil electrode 132, and/or the SVC coil electrode 134. As noted above, the case 400 may act as an active electrode in combination with the RV electrode 132, or as part of a split electrical vector using the SVC coil electrode 134 or the left atrial coil electrode 126 (i.e., using the RV electrode as a common electrode).

Cardioversion shocks are generally considered to be of low to moderate energy level (so as to minimize pain felt by the patient), and/or synchronized with an R-wave and pertain to the treatment of tachycardia. Defibrillation shocks are generally of moderate to high energy level (i.e., corresponding to thresholds in the range of, e.g., 5-40 joules), delivered asynchronously (since R-waves may be too disorganized), and pertain exclusively to the treatment of fibrillation. Accordingly, the microcontroller 420 is capable of controlling the synchronous or asynchronous delivery of the shocking pulses.

More generally, the exemplary device 100 can be programmed to stimulate different sets of vascular and cardiac muscles through the same lead/electrode system. The exemplary device 100 can be programmed to vary the output voltage of various pulses to effectively stimulate different muscles of the heart and blood vessels, even though the lead and electrode placement does not change.

Exemplary Cardiovascular Controller

Figure 5:
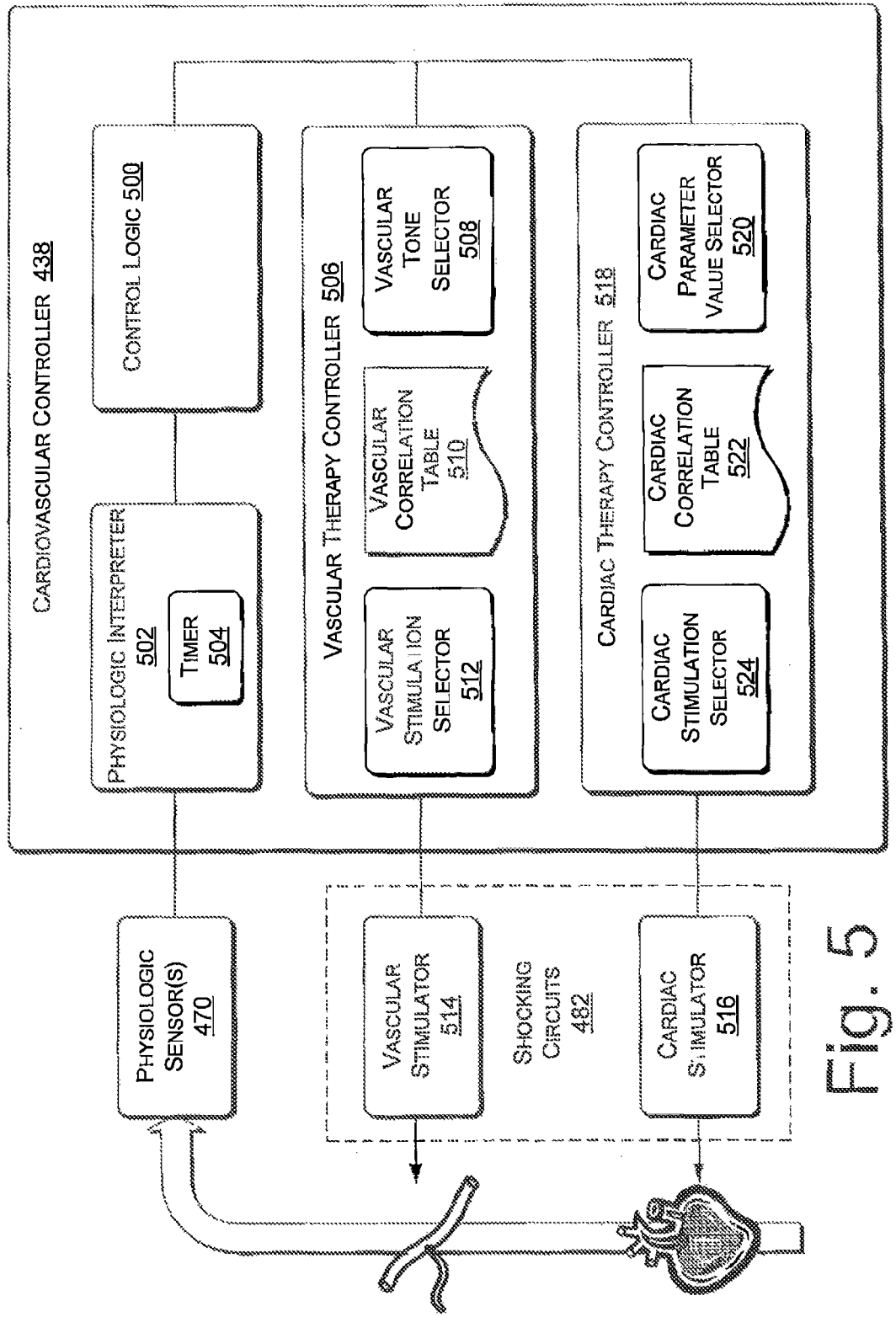
FIG. 5 is a block diagram of an exemplary cardiovascular controller of the exemplary implantable device.

FIG. 5 shows an exemplary cardiovascular controller 438 that can be implemented in an implantable medical device, such as device 100. The components of a cardiovascular controller 438, communicatively coupled with each other and with control logic 500, can be implemented in software, hardware, firmware, etc., or combinations thereof.

As mentioned, cardiovascular controller 438 has access to or includes physiological sensors 470. The physiological sensors 470 selected for a given implementation depend on the condition being treated. If the condition is orthostatic hypotension, then an activity/position sensor 471 that likely includes accelerometers may be included. A blood pressure sensor 473 and/or blood pressure probe may be included. A physiologic interpreter 502 can receive input from the physiological sensors 470 and interpret the input to diagnose a condition to be treated. The physiologic interpreter 502 provides feedback regarding changes in the condition being treated to the cardiovascular controller 438 and thereby provides information regarding the efficacy of therapies being provided by the cardiovascular controller 438. A timer 504 is included in the physiologic interpreter 502 to measure changes in the condition being treated and/or the efficacy of therapy over a time interval.

An exemplary vascular therapy controller 506 included in the cardiovascular controller 438 receives physiological information from the physiologic interpreter 502 and alters vascular stimulation responsively. Since the timer 504 can allow detection of physiological changes over very short time intervals, the vascular therapy controller 506 can dynamically match a given vascular therapy to changing conditions in near real time. For example, if a blood pressure sensor updates its readout approximately every 100 milliseconds, then the vascular therapy controller 506 can follow the blood pressure changes with an algorithm that changes vascular stimulation in proportion to changes in blood pressure, many times per second.

In one implementation, the vascular therapy controller 506 includes a vascular tone selector 508, a correlation table 510, and a stimulation selector 512. Vascular tone refers to a degree of vasoconstriction or vasodilation. The vascular tone selector 508 aims to select or calculate a degree of vascular tone that compensates or is therapeutic for a given condition. If the condition being treated is hypotension, then the vascular tone selector 508 seeks to increase blood pressure by promoting vasoconstriction. If the condition being treated is hypertension, however, then the vascular tone selector 508 may seek to decrease blood pressure by attenuating or foregoing vascular stimulation.

The correlation table 510 associates a physiological change in state determined by the physiologic interpreter 502 with a therapeutic response. For example, a sudden drop in blood pressure may be correlated with a particular voltage for stimulating a compensatory vascular response. Likewise, a particular vasomotor response selected by the vascular tone selector 508 may be correlated with stimulation parameters capable of achieving the vasomotor response. If the correlation table 510 does not yield vascular stimulation parameters directly, then a stimulation selector 512 may be included to convert a correlation intermediate to definite electrical quantities for performing the vascular stimulation. In other words, there may be a chain of related intermediate parameters between a physiological change detected by the physiologic interpreter 502 and the actual electrical quantities to be applied as responsive therapy for the physiological change.

In one implementation, the vascular correlation table 510 is included in or replaced by a correlation engine that executes an algorithm relating a detected physiological change to parameters for executing a vascular stimulation therapy. In another implementation, the vascular therapy controller 506 solves an equation at regular intervals in which a physiological variable on one side of the equation is proportional to a stimulation parameter on the other side of the equation. In yet another implementation, the vascular tone selector 508 and/or the vascular stimulation selector 512 may be excluded if their functions can be incorporated into a vascular correlation table 510 that is complete enough, e.g., that contains precalculated relationships between multiple intermediate variables.

Once the vascular therapy controller 506 selects stimulation parameters, a vascular stimulator 514 applies the stimulation to target tissue. If the target tissue is the greater splanchnic nerve 200, then electrical pulses may be applied through a vascular stimulation lead 112 and a cuff electrode 142. In the exemplary device 100, the shocking circuits 482 may include the vascular stimulator 514 as well as a cardiac stimulator 516.

Some implementations of the cardiovascular controller 438 may also include a cardiac therapy controller 518. In one implementation, the cardiac therapy controller 518 responds independently to feedback from the physiologic interpreter 502. In another implementation the cardiac therapy controller 518 determines a therapy based on the stimulation parameters determined by the vascular therapy controller 506. In yet another implementation, the cardiac therapy controller 518 considers input from both the physiologic interpreter 502 and the vascular therapy controller 506 in determining a cardiac therapy. The cardiac therapy controller 518 augments the vascular stimulation of the vascular therapy controller 506 in achieving a cardiovascular treatment or in some cases the two controllers (506, 518) work in concerted interdependence on each other.

A cardiac therapy controller 518 typically monitors cardiac activity through conventional components of a host ICD or even via components of a physiologic interpreter 502. Even so, the cardiac therapy controller 518 is not identical to a conventional ICD (e.g., for pacemaking) although functionality of the two may greatly overlap in some cases, especially when a cardiac therapy controller 518 utilizes the resources of an ICD to perform its functions. The cardiac therapy controller 518 can sometimes be differentiated from conventional ICDs in that the cardiac therapy controller 518 is more narrowly focused on the same cardiovascular treatment goal as the vascular therapy controller 506 and the stimulation parameter values selected by the cardiac therapy controller 508 are often derived from or interdependent on the stimulation parameter values selected by the vascular therapy controller 506. In other words, the two controllers (506, 518) team up to treat a specific cardiovascular condition using interdependent cardio and vascular stimulation parameters.

The cardiac therapy controller 518 may include a cardiac parameter value selector 520 (e.g., a heart rate selector) that proposes a value for a cardiac parameter to augment the compensatory vascular stimulation arrived at by the vascular therapy controller 506. The cardiac parameter value may also be selected in response to feedback provided by the physiologic interpreter 502, as discussed above.

The cardiac therapy controller 518 may include a cardiac correlation table 522 and a cardiac stimulation selector 524. These two components function analogously to the vascular correlation table 510 and the vascular stimulation selector 512 discussed above, namely, they translate a cardiac therapy enjoined in order to augment a vascular therapy into specific values of electrical parameters for applying cardiac stimulation. Like the vascular therapy controller 506 discussed above, in one implementation the cardiac parameter value selector 520 and/or the cardiac stimulation selector 524 may be excluded. This occurs if their functions can be incorporated into a cardiac correlation table 522 that is comprehensive enough to include precalculated relationships between related intermediate parameters that link the physiological condition being treated to values for electrical parameters for applying the augmentative cardiac stimulation.

The cardiac correlation table 522 and other components may be replaced by an engine that runs an exemplary cardiac correlation algorithm, relating a proposed cardiac response to the electrical quantities that can effect the response. In general, the cardiac therapy controller 518 is responsive to ongoing changes in the cardiovascular condition being treated and is also dynamically responsive to the ongoing adjustments being made by the vascular therapy controller 506.

Figure 6:
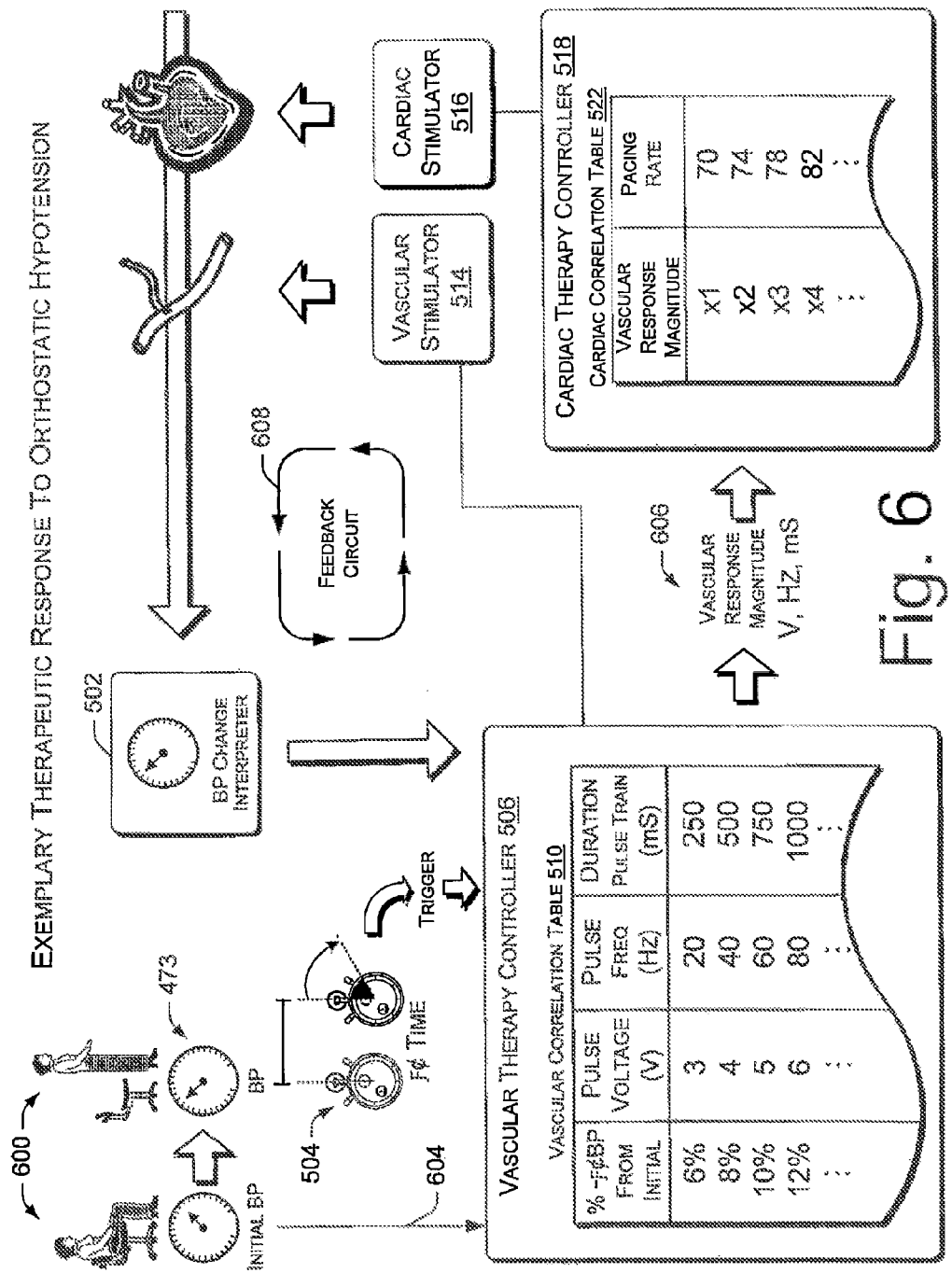
FIG. 6 is a diagram illustrating an exemplary therapeutic response by the exemplary implantable device to orthostatic hypotension.

FIG. 6 shows an exemplary therapy responsive to orthostatic hypotension. The therapy is provided by components of an exemplary device 100 depicted in FIGS. 1-5. Specifically, a cardiovascular controller 438 as depicted in FIG. 5 provides a response to an initial detection of orthostatic hypotension and thereafter dynamically tailors the ongoing therapy to subsequent changes in the orthostatic hypotension.

When a susceptible person 600 assumes a bodily position of increased verticality with respect to gravity, the emerging (higher) hydrostatic column of bodily fluids is influenced by the pull of gravity faster than bodily reflexes can compensate, resulting in a sudden drop in intracranial blood pressure. The change in bodily position may be detected by an accelerometer or activity/position sensor 471 in the device 100 and the decrease in blood pressure may be detected by a physiological sensor 140, by a blood pressure sensor 473, and/or physiologic interpreter 502. A timer 504 may commence a measurement interval (for example, half a second) at the end of which the blood pressure is reevaluated. If the blood pressure is still unsatisfactory, then the device 100 may intervene at the end of the time interval, i.e., before the susceptible person 600 faints. The combination of detecting a qualifying body position and a sudden decrease in blood pressure sustained over the time interval provides a trigger for activating the vascular therapy controller 506.

In an example of a vascular correlation table 510, the illustrated implementation depicts a family of precalculated relationships between possible changes in the physiological condition being treated and corresponding values for electrical parameters. The values for each set of electrical parameters represent controlled responses to be used for applying electro-stimulation to a sympathetic nerve, e.g., to the greater splanchnic nerve 200, in order to elicit rapid global vasoconstriction that mimics a healthy baroreceptor reflex. Upon assuming a more upright position, if the systolic blood pressure of the susceptible person 600 drops from, e.g., 120 mmHg to 110 mmHg (an 8% decrease), and the lower blood pressure reading is sustained for a requisite time interval, then the vascular therapy controller 506 is triggered and the vascular correlation table 510 is referenced at the entry or record for the 8% decrease in blood pressure.

In the shown implementation, percentage changes in blood pressure are correlated directly with values for electrical parameters for stimulating the greater splanchnic nerve 200. For example, in a given susceptible person 600, an orthostatic hypotension episode with an initial blood pressure drop of 8% may call for a therapy consisting of a train of sympathetic electro-pulses in which the train includes three volt pulses of one millisecond duration each that have an energy of one hundred nanojoules apiece, applied to the greater splanchnic nerve 200 at a frequency of twenty pulses per second (Hz); the train of pulses lasting 250 milliseconds. This would apply a train of approximately four pulses before the occurrence of a subsequent reevaluation of blood pressure using feedback from the physiologic interpreter 502.

If the initial drop in blood pressure is greater than 8%, then the vascular therapy controller may begin treatment with a greater vascular response magnitude (i.e., higher voltage, higher frequency, and/or longer pulse train). Then, as the applied therapy has its beneficial effect the vascular therapy controller 506 adjusts treatment by referencing the vascular correlation table 510 at the entry or record of the current value of blood pressure change—provided as feedback by the physiologic interpreter 502. It should be noted that the percentage change calculation may use an initial blood pressure value 604 for the calculations.

The magnitude of a vascular therapy response can be fed as input to the cardiac therapy controller 518. It should be noted that some implementations of the cardiovascular controller 438 do not include a cardiac therapy controller 518 at all. The cardiac correlation table 522 relates the input vascular response magnitude 606 to a value for a cardiac parameter in order to create a cardiac stimulation that augments or is synergistic with the vascular stimulation to be applied (or already being applied).

For example, a slight drop in blood pressure might elicit values for electrical parameters from the vascular therapy controller 506 that correlate with a cardiac pacing rate of 70 beats per minute—to be used if the native pulse rate is below this nominal value. The value for proposed pacing rate might increase in conjunction with proposed increases in the vascular response magnitude 606.

The vascular and cardiac stimulation values are passed respectively to the vascular stimulator 514 and to the cardiac stimulator 516, and thence to the respective tissues. The stimulation therapies applied have a physiological effect or lack thereof that is detected by the physiologic interpreter 502 (in this case, a blood pressure change interpreter). The detected physiological changes are provided as feedback to the vascular therapy controller 506, as already discussed, to forge a subsequent vascular response, that is, an adjustment of the therapy. Thus, the various phases of the example therapeutic response to orthostatic hypotension comprise a self-regulating feedback circuit 608 that dynamically adjusts itself to cover whatever changes happen in the physiological condition being treated.

In an alternative implementation, a cardiovascular controller 438 is programmed to provide vascular stimulation via a sympathetic nerve for improving circulation in bedridden and inactive persons. A vasoconstriction response is nearly instantaneous when the vascular stimulator 514 applies pulses to the greater splanchnic nerve 200 (e.g., the above-mentioned indirect releases of epinephrine are known to have a global effect on blood vessels that is nearly instantaneous—that is, each release is a tiny "adrenaline rush"). Bursts of vascular stimulation pulses can be timed to coincide with one or more points or segments in the cardiac cycle in order to reinforce blood circulation, especially in the lower limbs of a person who is bed-bound. It is well known that the contraction of leg muscles used during ambulation assists the pumping action of the heart, especially by pushing blood through venous valves. This alternative implementation augments the pumping action of the heart in an inactive person. A similar implementation may treat persons afflicted with diastolic heart failure.

In the above-described alternative implementation, the physiologic interpreter 502 may monitor the cardiac cycle and the implementation times a vascular stimulation burst to coincide with a segment of the cardiac cycle at which systole is waning into diastole. At this or some other cardiac segment determined by trial-and-error (as their may be some lag in the responsiveness of the vascular system), the vascular therapy controller 506 applies pulses so that vasoconstriction occurs just as blood pressure is dropping between systole and diastole—to give the contraction of elastic arterial walls an extra boost. This provides an extra motor for circulation in the lower limbs of an inactive person by augmenting venous return.

Exemplary Methods

Figure 7:
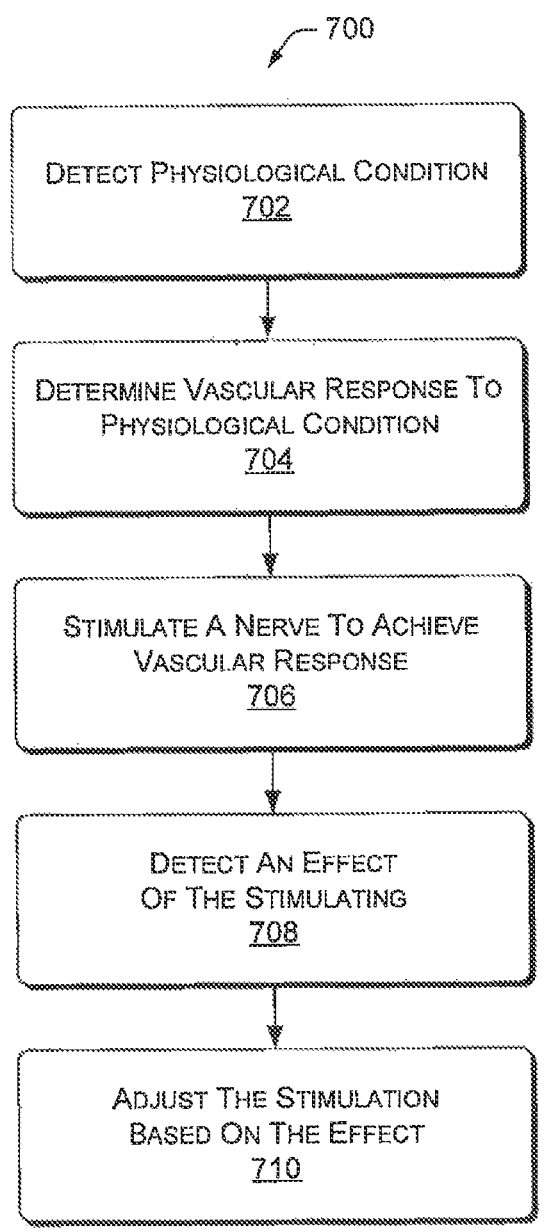
FIG. 7 is a flow diagram of an exemplary process for providing responsive vascular therapy.

FIG. 7 shows an exemplary process 700 for dynamically providing a vascular response to one or more physiological conditions. This process 700 may be implemented in connection with any suitably configured device, although it will be described as being executed by the exemplary implantable device 100 of FIGS. 1-6. In the flow diagram of FIG. 7, the operations are summarized in individual blocks. The operations may be performed in hardware and/or as machine-readable instructions (software or firmware) that can be executed by a processor, such as microcontroller 420.

As described above, a host of physiological conditions may benefit from a responsive vascular therapy. Accordingly, at block 702, at least one physiological condition is detected. The physiological condition(s) may be circumstances that trigger a cardiovascular controller 438 to take responsive action. For example, detecting a bodily movement into a more upright position coupled with a sudden drop in blood pressure sustained over an interval may trigger a vascular therapy for orthostatic hypotension.

A physiologic interpreter 502 may be employed to detect physiological conditions or changes relevant to therapy. For example, a period of lower limb inactivity that exceeds a set threshold may trigger an ongoing detection of a segment of the recurring cardiac cycle. Each time the repeating segment of the cardiac cycle is detected, the vascular therapy controller 506 stimulates vasoconstriction to augment pumping of blood in the limbs.

At block 704, a magnitude of a vascular response to the detected physiological condition or change is determined. A vascular response of vasoconstriction may be achieved by electrically stimulating a sympathetic nerve, but achieving a vascular response of vasodilation by electrically stimulating a parasympathetic nerve could also be employed in some implementations. A vascular correlation table 510 may relate a magnitude of the physiological condition or change to a magnitude of a vascular response. In other implementations, the relation between a physiological condition and a vascular response may be determined algorithmically or calculated in real time by an engine.

Since the stimulation is typically by electrical pulses, e.g., via leads of the device 100, the values of the electrical parameters are determined as part of determining the vascular response. A vascular stimulation selector 512 may determine voltage, energy, and duration of pulses to be applied as well as frequency of pulses and duration of a train of pulses. The vascular stimulation selector 512 may also determine whether to apply the pulses as a pulse train or in bursts.

At block 706, stimulation for achieving the vascular response is applied to a nerve. An exemplary nerve for achieving vasoconstriction on a systemic level is the greater splanchnic nerve 200 which innervates the abdominal splanchnic vascular bed and the adrenal glands. This vascular bed is thought to be one of the major effectors used by the baroreceptor reflex for achieving an increase in blood pressure. Not only does stimulation of this nerve cause massive vasoconstriction of abdominal blood vessels, but it also appears to actuate a release epinephrine from the adrenals, that further produces global vasoconstriction as well as bronchodilation and other effects of sympathetic stimulation.

At block 708, a physiological effect or result of providing a vascular response is detected. A physiologic interpreter 502 includes or has access to physiologic sensors 470 for the detection. The physiological result to be detected should have some relevance to the physiological condition being treated by the device 100.

At block 710, the vascular response is dynamically adjusted based on the effect detected at block 708. In other words, the vascular therapy controller 506 and the physiologic interpreter 502 are components of a feedback circuit that is similar to the body's own feedback mechanisms for maintaining homeostasis. An adjusted therapy, of course, is usually proportional to the detected change in a physiological condition. Thus, the provided vascular therapy backs off as the condition improves.

Figure 8:
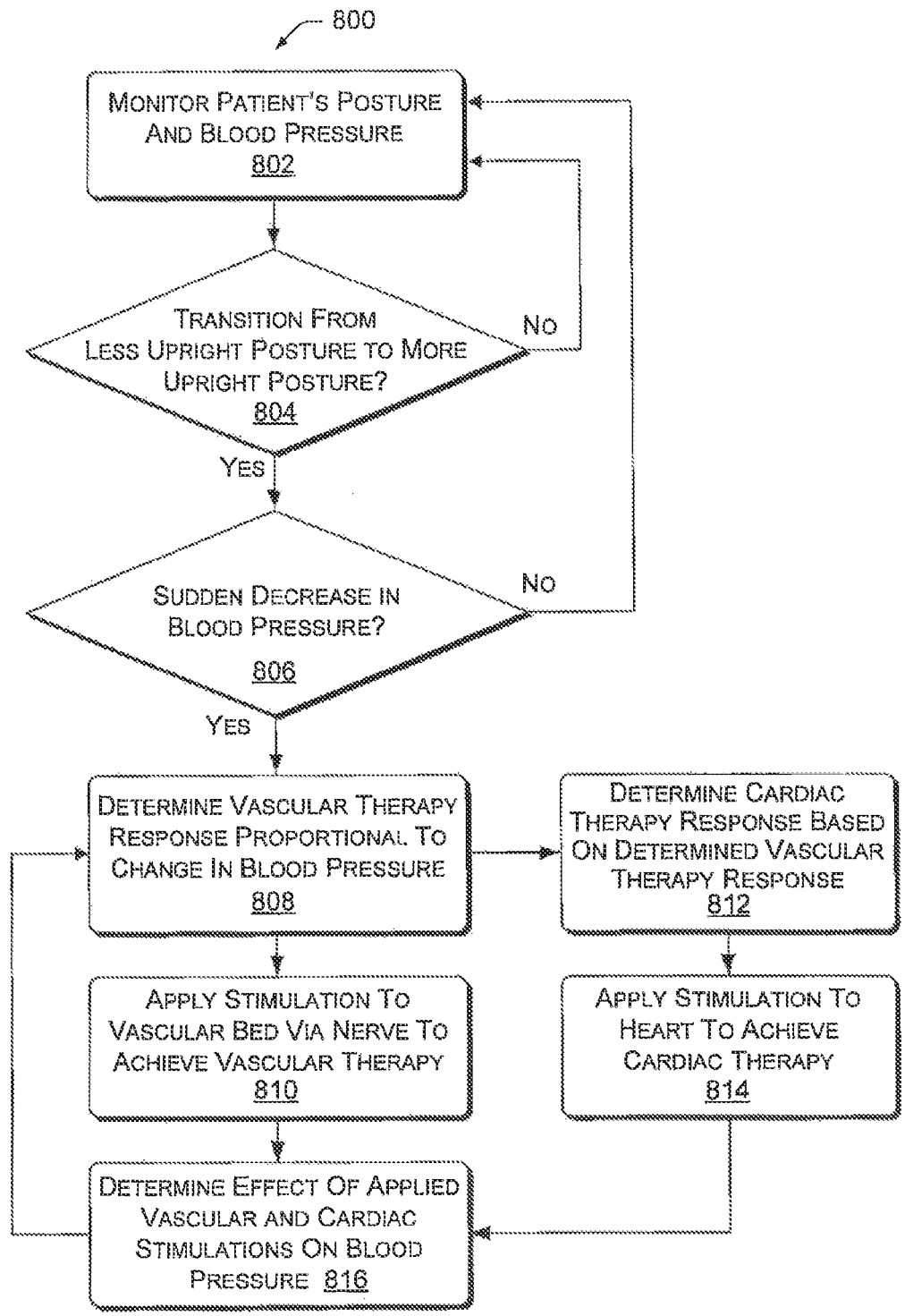
FIG. 8 is a flow diagram of an exemplary method of providing responsive cardiovascular therapy for orthostatic hypotension.

FIG. 8 shows an exemplary process 800 for dynamically providing a vascular response to orthostatic hypotension. This process 800 may be implemented in connection with a suitable device, although herein it is described as being executed by the exemplary implantable device 100 of FIGS. 1-6. In the flow diagram of FIG. 8, the operations are summarized in individual blocks. The operations may be performed in hardware and/or as machine-readable instructions (software or firmware) that can be executed by a processor, such as microcontroller 420.

At block 802, the device 100 may perform ongoing monitoring of bodily position and blood pressure, or may have the capacity to activate a blood pressure sensor if body position meets certain criteria. At block 804, in order to check for triggering circumstances, the method 800 checks for a recent posture change to a more upright position. If such a qualifying change in body position has occurred, then at block 806 the method 800 checks for a concomitant sudden decrease in blood pressure of at least 10 mmHg. If the blood pressure drop is sustained over a time interval during which a healthy baroreceptor response would have intervened to restore satisfactory blood pressure, then at block 808 the method 800 determines a vascular therapy response that is proportional to the magnitude of the triggering change in blood pressure. At block 810, the vascular therapy determined at block 808 is applied, e.g., as a train of electrical pulses, to the greater splanchnic nerve 200 to effect a vasoconstrictive response. The duration of the therapy applied determines when a subsequent evaluation of the effectiveness of the therapy will be performed.

At block 812, the method 800 may additionally determine a cardiac therapy based on the vascular therapy determined at block 808. When the method 800 is executed by device 100, then in some implementations a cardiac therapy controller 518 is subservient to a vascular therapy controller 506. That is, the values of the electrical and timing parameters for a cardiac stimulation response are derived from the values of the electrical and timing parameters determined for a vascular stimulation response. At block 814, the cardiac therapy determined at block 812 is applied, e.g., as cardiac pacing pulses, to the heart to augment the vasoconstrictive response being applied at block 810. The length of the therapy applied determines when a subsequent evaluation of the effectiveness of the therapy will be performed and generally matches the duration of the vascular therapy.

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

What is claimed is:

1. A non-transitory medium readable by a microcontroller of an implantable stimulation device, containing instructions that when executed cause the implantable stimulation device to perform actions, including:
   detecting a sudden and sustained change in blood pressure;
   relating the change in blood pressure to vascular stimulation parameters for executing a vascular therapy;
   directly electrically stimulating a sympathetic nerve to achieve the vascular therapy using said vascular stimulation parameters;
   determining a cardiac response to the change in blood pressure based on said vascular stimulation parameters;
   correlating the cardiac response to cardiac stimulation parameters that can effectuate the cardiac response;
   electrically stimulating a heart to achieve the cardiac response using the cardiac stimulation parameters;
   detecting an effect of the stimulation of the sympathetic nerve and the heart;
   adjusting stimulation parameters for stimulating the sympathetic nerve and the heart based on the effect; and
   stimulating the sympathetic nerve and the heart using the adjusted stimulation parameters.

2. The non-transitory medium as recited in claim 1, wherein relating the change in blood pressure to vascular stimulation parameters for executing a vascular therapy comprises executing an algorithm relating the change in blood pressure to parameters for executing a vascular therapy.

3. The non-transitory medium as recited in claim 1, wherein relating the change in blood pressure to vascular stimulation parameters for executing a vascular therapy comprises using a correlation table that associates a change in blood pressure with stimulation parameters for executing a vascular therapy.

4. The non-transitory medium as recited in claim 1, wherein the correlation table contains precalculated relationships between multiple intermediate variables.

5. The non-transitory medium as recited in claim 1, wherein the instructions that when executed perform actions, further include determining subsequent changes in blood pressure at regular intervals and relating at regular intervals said changes in blood pressure to vascular stimulation parameters for executing a vascular therapy.

6. The non-transitory medium as recited in claim 1, wherein the vascular stimulation parameters comprise at least one of a voltage, energy, duration of pulses, frequency of pulses, trail of pulses, burst, and a duration of a train of pulses.

7. The non-transitory medium as recited in claim 1, wherein the vascular therapy comprises a degree of vasoconstriction to compensate for the change in blood pressure.

8. The non-transitory medium as recited in claim 1, wherein said stimulating a sympathetic nerve comprises providing electrical pulses to a greater splanchnic nerve to substitute for a baroreceptor reflex response to orthostatic hypotension.

9. The non-transitory medium as recited in claim 1, wherein said vascular stimulation parameters include electrical parameters for a pulse train to be applied to the greater splanchnic nerve, wherein the electrical parameters include a pulse voltage, a pulse energy, a pulse duration, and a number of pulses in the pulse train.

10. The non-transitory medium as recited in claim 1, wherein said detecting an effect of the stimulation of the sympathetic nerve and the heart comprises detecting a subsequent change in blood pressure.

11. The non-transitory medium as recited in claim 1, wherein said adjusting stimulation parameters for stimulating the sympathetic nerve and the heart based on the effect comprises adjusting one or more electrical parameters for a pulse train to be applied to the greater splanchnic nerve.

12. The non-transitory medium as recited in claim 1, wherein the cardiac response comprises a cardiac pacing rate to augment said stimulating the sympathetic nerve.

13. The non-transitory medium as recited in claim 1, further comprising detecting a recurring segment of a cardiac cycle.

14. An implantable stimulation device comprising:
   at least one pulse generator configured to produce one or more stimulation pulses; and
   a microcontroller configured to:
      detect a sudden and sustained change in blood pressure;
      relate the change in blood pressure to vascular stimulation parameters of the at least one pulse generator for executing a vascular therapy;
      direct electrically stimulating a sympathetic nerve to achieve the vascular therapy using said vascular stimulation parameters;
      determine a cardiac response to the change in blood pressure based on said vascular stimulation parameters;
      correlate the cardiac response to cardiac stimulation parameters of the at least one pulse generator that can effectuate the cardiac response;
      initiate electrical stimulation of a heart to achieve the cardiac response using the cardiac stimulation parameters;
      detect an effect of the stimulation of the sympathetic nerve and the heart;
      adjust the stimulation parameters of the at least one pulse generator for stimulating the sympathetic nerve and the heart based on the effect; and
      trigger the pulse generator to generate one or more stimulation pulses using the adjusted stimulation parameters.

15. The implantable device of claim 14, wherein the microcontroller comprises a correlation engine that is configured to execute an algorithm relating a change in blood pressure to parameters for executing a vascular stimulation therapy.

16. The implantable device of claim 14, wherein the microcontroller comprises a correlation table that associates a change in blood pressure with stimulation parameters for executing a vascular therapy.

17. The implantable device of claim 14, wherein the sympathetic nerve comprises a greater splanchnic nerve.

18. The implantable device of claim 14, wherein the effect of the stimulation of the sympathetic nerve and the heart comprises a subsequent change in blood pressure.

19. The implantable device of claim 14, wherein the cardiac response comprises a cardiac pacing rate to augment said stimulating the sympathetic nerve.

20. The implantable device of claim 14, wherein the microcontroller is further configured to detect a recurring segment of a cardiac cycle.

* * * * *